United States Patent [19]
Chanock et al.

[11] 3,992,522
[45] Nov. 16, 1976

[54] TEMPERATURE-SENSITIVE RECOMBINANT MUTANT VIRUSES AND A PROCESS FOR PRODUCING SAME

[75] Inventors: Robert M. Chanock; Brian R. Murphy, both of Bethesda, Md.

[73] Assignee: The United States of America as represented by the Department of Health, Education and Welfare, Washington, D.C.

[22] Filed: June 18, 1975

[21] Appl. No.: 587,974

Related U.S. Application Data

[63] Continuation-in-part of Ser. No. 326,554, Jan. 24, 1973, abandoned.

[52] U.S. Cl. ................................ 424/89; 195/1.4
[51] Int. Cl.² .................... A61K 39/18; C12K 7/00
[58] Field of Search ..................... 195/1.4; 424/89

[56] References Cited
OTHER PUBLICATIONS
Brdar et al., Chem. Abst., vol. 79 (1973) p. 13954v.

Primary Examiner—Sam Rosen
Attorney, Agent, or Firm—John S. Roberts, Jr.; Norman J. Latker; Thomas G. Ferris

[57] ABSTRACT

A method and resulting temperature sensitive (ts) recombinants which may be produced by modifying wild-type influenza A viruses by utilization of chemically mutagenized donor viruses possessing ts lesions and shut off temperatures in the area 37°–38° C. Such a recombinant virus has been produced that contains the surface H3 antigen of influenza A/Hong Kong/1968 (H3N2) virus and a temperature-sensitive (ts) lesion derived from a ts mutant of influenza A/Great Lakes/1965 (H2N2) virus. Additional donor viruses include influenza A/Hong Kong/1968-ts-1[A], influenza A double recombinant 10B, and influenza A/Hong Kong/1968-ts-1[E]. When utilized as a vaccine, these temperature-sensitive recombinant viruses have the facility to develop only mild symptoms, but the infection induces complete resistant to influenzal disease produced by challenge with a virulent wild-type virus. The temperature-sensitive donor mutant is prepared chemically by growth of the virus in the presence of 5-fluorouracil (5-FU).

5 Claims, No Drawings

TEMPERATURE-SENSITIVE RECOMBINANT MUTANT VIRUSES AND A PROCESS FOR PRODUCING SAME

This is a continuation-in-part of abandoned application Ser. No. 326,554, filed Jan. 24, 1973, of Robert M. Chanock and Brian R. Murphy.

The present invention relates to a live virus vaccine for the prevention of influenzal disease. Traditionally, inactivated vaccine has been used for prevention of influenzal disease in the United States and elsewhere. However, a live vaccine like the present invention continues to offer a number of potential advantages, of which probably the most important centers on the local immune defense mechanisms of the respiratory tract. In facilitating the present invention, conditional-lethal, temperature-sensitive (ts) mutants of the following influenza A type viruses were produced:

Influenza A/1965-ts-1 (H2N2)
Influenza A/Hong Kong/1968-ts-1[A] (H3N2)
Influenza A Double recombinant 10B (H0N2)
Influenza A/Hong Kong/1968-ts-1[E] (H3N2)

and further recombinant viruses were prepared such as one denoted ts-1[E] which was produced from wild-type influenza A/Hong Kong/ 1968 (H3N2) and the 1965-ts-1 mutant noted above. These recombinant viruses were found satisfactory against specific challenge or challenges by wild-type virus.

The term temperature-sensitive (ts) mutation affords the possibility of site-specific attenuation for the lower respiratory tract. The acquisition of temperature-mutant defects in a strain of influenza virus has been shown in mice to be associated with diminished virulence, though the antibody producing stimulus remained (*British Medical Journal*, 1969, 3:757-758). Replication of mutants with markedly restricted growth at 37°C—38° C appears to be greatly limited in the lower respiratory tract, the major site of significant pathology, which has a temperature of 37° C. However, the mutants should grow with reasonable efficiency in the cooler passages of the upper respiratory tract, which have a temperature of 32° – 34° C. In this manner, ts mutants grow primarily in the upper respiratory tract and stimulate immunologic defense mechanisms without producing symptoms in the lower tract. Additionally, ts mutants are often partially defective at permissive temperatures (32°–34° C), and this property offers the possibility of attenuation for the upper respiratory tract as well.

The prior art relative to the present invention is of the literature variety. From the publications of the present research group:

Murphy, et al, "Temperature-Sensitive Mutants of Influenza Virus. II. Attenuation of ts Recombinants for Man," *The Journal of Infectious Diseases*, Vol. 126, No. 2, August 1972, pages 170–178.

Murphy, et al., "Temperature Sensitive Mutants of Influenza Virus. III. Further Characterization of the ts-1[E] Influenza A Recombinant (H3N2) Virus in Man," *J. of Infectious Diseases*, 128:479-487, 1973.

PUblications of other researchers:

Beare, et al., "Recombinant Influenza-A Viruses as Live Vaccines for Man," *Lancet*, 2:1271-1273, 1971. This Beare journal article does refer, as the title indicates, to a recombinant influenza-A virus as live vaccines for man; however, at page 1272, Table 2, it shows that there is no correlation between restricted growth at 39° and attenuation. This is brought out by the notation that the virulent parent virus (939) is restricted to 39° and the attenuated virus (PR8) replicates well at 39°. Additionally, clone 7 grows well at high temperature and is virulent, whereas clone 64C similarly grows well at 39° but it attenuated. Beare demonstrates simply that the mating of an avirulent virus (PR8) and a virulent virus (939) can give rise to clones of viruses with a spectrum of virulence for man. However, in this article there is no specific characteristic; i.e., temperature sensitivity, associated with this attenuation. The Beare article also utilizes an avirulent virus produced by serial passage in animal and tissue culture rather than by chemical mutagenesis.

Maassab, et al., "Hybrid Formation of Influenza Virus at 25° C," *Fed. Proc.*, 30:413, 1971 [abstract]. This immunology abstract and the parent article, *Proc. Soc. Exp. Biol. and Med.*, 139:768, March 1972, relate to the procedure of Dr. Maassab to produce attenuated viruses of influenza A virus, which is similar to but distinct from the present procedure. Maassab produces an attenuated parent virus by growth of virus at low temperature, a well-known technique for the production of live attenuated virus vaccine strains. Live measles vaccine have been produced in this manner. The present chemical technique involves the chemical mutagenesis of influenza A virus and the subsequent isolation of viruses that are temperature sensitive. The end result is to produce viruses that grow at 34° but not at 39°, and these are the ts attenuated viruses. The Maassab technique, which involves a transfer of a defect from an attenuated strain to a new wild-type virus by genetic recombination, is similar to the present invention, but the method of production of attenuated viruses is different.

MacKenzie, "Virulence of Temperature-Sensitive Mutants of Influenza Virus," *Br. Med. J.*, 3:757-578, 1969. With reference to this MacKenzie article, it is noted that distinct from the present development, MacKenzie did not work with recombinant ts viruses, although he did demonstrate the ts mutants of influenza A viruses produced by chemical mutagenesis were attenuated for animals. More important, the virus preparations in the journal article were not suitable for human use and no attempt was made to pass these ts defects to different influenza A viruses by recombination.

In general, the present method and resulting product lie in a method for producing a temperature sensitive (ts) recombinant mutant produced by growth of an influenza A virus in the presence of 5-fluorouracil to produce a chemically mutagenized and temperature-sensitive virus which is the donor of a defined genetic defect and which is mated with a virulent wild-type A virus of a different antigenic type to produce the new recombinant antigenic-type virus.

The following donor viruses have been utilized as vaccine material when mated with a wild-type influenza A virus. One virus, influenza A/Hong Kong/1968-ts-1[A] (H3N2), possesses two ts lesions--one in genetic group 1 and the other in genetic group 5. The other donors are the influenza A/Double recombinant 10B virus and influenza A/Hong Kong/ts-1[E] virus.

TABLE 1

| Virus Designation | Antigenic Characterization | Genetic Group | Shut Off Temp. |
|---|---|---|---|
| Influenza A/Hong Kong/ | H3N2 | 1,5 | 37° C |

TABLE 1-continued

| Virus Designation | Antigenic Characterization | Genetic Group | Shut Off Temp. |
| --- | --- | --- | --- |
| 1968-ts-1[A] Influenza A Double recombinant 10B | H0N2 | 1,4 | 38° C |
| Influenza A/Hong Kong/ 1968-ts-1[E] | H3N2 | 1,2 | 38° C |

THE PREPARATION OF RECOMBINANT VIRUSES CONTAINING A SURFACE H3 ANTIGEN OF INFLUENZA A/HONG KONG/1968 (H3N2) VIRUS AND A TEMPERATURE- SENSITIVE (ts) LESION DERIVED FROM A ts MUTANT OF INFLUENZA A/GREAT LAKES/1965 (H2N2) VIRUS

The Starting Material

Influenza $A_2$/0389/1965 in its third and twenty-first bovine kidney (BK) passages at 36° C (BK-3, BK-21) was obtained from Abbott Laboratories, North Chicago, Illinois. The BK-21 viral suspension was passaged once in BK on receipt at NIH and the resulting BK-22 viral suspension was used as starting material for the selection of mutants.

Preparation of the Temperature-Sensitive (ts) Mutant of Influenza A/Great Lakes/1965 (H2N2)

The ts mutant was prepared by growth of virus in the presence of 5-fluorouracil (5-FU) according to the procedure of MacKenzie, J. Gen. Virol., 6:63–75, 1970. One mutant, ts-1, failed to produce plaques at or above 37° C. It was also found that the mutant was genetically stable in vitro and was restricted in its growth in the hamster's lower respiratory tract. In animal studies the mutant grew poorly in the lungs but induced significant resistance as in hamsters to subsequent challenge with wild-type virus. It was finally observed that the mutant was found to possess a distinct genetic lesion from the influenza A (H2N2)-ts-2 virus.

Isolation of Mutants

Starting with a viral suspension at the twenty-second passage level (BK-22), a genetically homogeneous suspension of virus was prepared at the twenty-seventh passage level by triple plaque-to-plaque purification at 37° C. Mutants were produced by growth of virus (at the twenty-eighth passage level) in BK cells maintained with medium containing 3 mM 5-fluorouracil. This produced > 99% inhibition of viral growth at 48 hr. Approximately 350 plaques formed by virus which had grown for 48 hr. in the presence of 5-fluorouracil were picked, and these viral populations were passaged once in BK roller-tube culture before being tested for the presence of the ts property by simultaneous titration at 32° C and 38° C. This additional passage was necessary because individual plaques contained too few pfu to provide meaningful data. Of the 350 plaques, 42% yielded viable virus, and two of the progeny exhibited a decreased titer at 38° C compared with that at 32° C. Viruses from these two plaques were subjected to double-to-plaque purification at 32° C before stock suspension of virus was prepared at the BK-35 and BK-36 passage levels; in addition, a plaque derived from unmutagenized virus was also passaged and plaque-purified in a similar manner as a control.

The Product

A recombinant of the present invention was produced during mixed infection of primary bovine-kidney (BK) cells with wild-type influenza A/Hong Kong/1968 (H3N2) virus and influenza A/Great Lakes/1965 (H2N2) ts-1 mutant.

Additional procedures included the utilization of egg grown virus which also achieved an acceptable balance between attenuation and immunogenicity. It was found further that the product ts-1[E] was a poor stimulator of antineuraminidase antibody, and, in this respect, the ts virus behaves similar to the wild type in man.

The recombinant, ts-1[E], appears to possess the desired degree of attenuation. This virus was sufficiently defective so that the majority of infected individuals did not develop symptoms. Symptoms that did occur were mild and were considered acceptable when balanced against the disease to be prevented. Infection with the recombinant was extensive enough, however, to stimulate a moderately high titer of neutralizing antibody in sera and nasal washings. The recombinant appears to be genetically stable during replication in the respiratory tract of man, and infection did not spread from infected individuals to susceptible cohorts despite close contact during a time when the former group shed virus.

It is believed theoretically that major shifts in surface antigens of human influenza A virus arise through recombination between an influenza A virus of man and one of avian or animal origin [Rasmussen, "Avia Myxoviruses and Man," Hanson (ed.), Newcastle Disease Virus, University of Wisconsin Press, 1964, pages 313–325; and Kilbourne, Science, 160:74–76, 1968]. This view is supported by the marked difference in protein structure exhibited by the hemagglutinins of the Asian (H2) and Hong Kong (H3) viruses.

The generalized method of production of temperature-sensitive recombinants involves a mixed infection of cells grown in tissue culture incubated at the permissive temperature (34° C) using two viruses: (1) a temperature-sensitive virus of one serotype and (2) another non-ts that one desires to attenuate. Antiserum to the ts virus must be available that will neutralize the ts parent virus but have no effect on the non-ts virus. The cells are infected simultaneously at a multiplicity of infection of 5 or greater with respect to each parent virus. The progeny of this mating is then plaqued on monolayer cultures at the permissive temperature in the presence of antisera to the ts parent virus. The virus present in the plaques is then inoculated into tissue culture, incubated at the permissive temperature, and harvested. The virus present in this harvest is then characterized for its serotype and temperature sensitivity. The virus which has both the serotype of the non-ts parent and the ts defect of the ts parent is considered to be the desired recombinant. The desired recombinant ts virus is then subjected to two successive plaque-to-plaque passages.

After the last plaque passage, the virus is then grown up in tissue culture and the serotype and ts characteristic again determined. This method of plaque-to-plaque purification insures that the recombinant virus is both genetically homogeneous and stable. The ts recombinant virus is ready at this point to be used as a seed for production of larger quantities of virus.

Recombinants were recovered by plating the progency from the mixed infection of influenza A/Great Lakes/1965 (H2N2) temperature sensitive virus and influenza A/Hong Kong/1968 (H3N2) virus onto BK monolayers in the presence of H2 antiserum and by characterizing the antigenic structure and ts phenotype of the resulting plaques. The genetically stable recombinant selected has the surface H3 antigen of the Hong Kong virus and a ts lesion or lesions of the 1965 influenza A virus.

The recombinants derived from the ts-1 mutant exhibited three different patterns of temperature sensitivity. Like the parent ts-1 mutant, one class of recombinants had a shut-off temperature of 375° C, while recombinants belonging to the other two classes had restrictive temperatures of 38° C and 39° C, respectively. It was believed that the ts-1 mutant contained three discreet ts lesions and that these were segregated during recombination with the influenza A/Hong Kong/1968 (H3N2) virus.

Of the three ts viruses recovered, two, namely, ts-1[A] and ts-1[E], were further investigated.

Suspensions of the two recombinants which were evaluated in man were prepared in primary bovine kidney culture, using an inoculum virus that had been purified by two successive plaque passages. The recombinants were in the 19th BK passage with respect to the H3N2 parent and in the 42nd BK passage with respect to the H2N2 parent. Tissue cultures were maintained with a mixture of Eagle's No. 2 medium and medium 199 supplemented with 0.5% gelatin but no antibiotics or serum.

Wild-Type Virus

Two suspensions of influenze A/1968 (H3N2) virus were prepared for challenge of human volunteers who had previously received one of the ts recombinants. The first strain was recovered in 1968 in primary human embryonic-kidney culture and passaged four times in primary BK culture; this virus originated from a specimen collected in Hong Kong (Van Kirk, et al, Proc. Soc. Exp. Biol. Med., 136:34–41, 1971). The second strain, originating from a specimen collected in Bethesda, Maryland, was recovered in primary human embryonickidney culture and was passaged once in this cell system. The two suspensions of wild-type virus were tested for adventitious agents and no contaminants were detected.

The viral suspensions grown in BK cultures were tested for adventitious microbial agents following the procedure of Knight, Progr. Med. Virol., 6:1–26, 1964, and additionally, each of the viral suspensions was tested (after 20-30 fold concentration) for the presence of reverse transcriptase (the enzyme associated with C-type RNA oncogenic viruses), using the synthetic polynucleotide oligothymidylic acid-polyriboadenylic acid, according to the method of Parks, et al., J. Virol., 9:110–115, 1972.

Measurement of Infectivity and Neutralizing Antibody

Infectivity of the recombinant and wild-type viruses was measured by the hemadsorption technique, using rhesusmonkey kidney roller-tube cultures, and the titers were expressed in 50% tissue culture infective doses ($TCID_{50}$). Neutralizing antibody was measured in simian BSC-1 tissue-culture tubes by the technique of Van Kirk et al., Proc. Soc. Exp. Biol. Med.; 136:34–41, 1971. Utilizing intranasal route of inoculation of the ts-1[E] virus, the human infective dose 50 was approximately $10^{5.0}$ $TCID_{50}$, and a dose of $10^{6.0}$ $TCID_{50}$ per person was an effective immunizing dose, with an immunizing range of from $10^{5.0} - 10^{7.0}$ $TCID^{50}$ per person.

EXAMPLE 1

Evaluation of the recombinant viruses and especially that of ts-1[E] were carried out through volunteers from correctional institutions in the Washington, D.C., area. In general, the men who participated in these studies were selected on the basis of general good health and titer of neutralizing antibody in serum for influenze A/Hong Kong/1968 (H3N2) of 1:8 or less. This value was considered to be seronegative.

The volunteers were housed in an isolation area for three days before and for ten days after administration of virus. The viral suspensions were delivered into the nose by a Devilbis No. 15 atomizer. Nasopharyngeal washes were collected daily and inoculated in 0.25 ml quantities into four rhesus-monkey kidney roller-tube cultures in an attempt to recover virus. Blood was collected for serologic studies before administration of virus and at weekly intervals for four weeks. Nasal washings were collected with saline on a similar schedule and concentrated by Aquacide. Concentrated nasal washings were adjusted to 20 mg of IgA/100 ml (determined with a serum IgA standard) before being tested for titer of neutralizing antibody in BSC-1 tissue cultures.

The volunteers were examined independently each day by two physicians. The following categories of illness were employed for the purpose of evaluating clinical response: (1) coryza (nasal, stuffiness, rhinorrhea, and sneezing); (2) coryza plus pharyngitis and malaise; (3) mild influenzal illness (coryza, pharyngitis, malaise plus two of the following: chills, sweating, photophobia, or headache); and (4) influenzal illness with cough and sputum.

Virus recovered from volunteers who were given the ts recombinants was studied for its efficiency of plaque formation (eop) at 32° and 39° C to determine whether viral replication in man led to the emergence of revertant, wild-type virus. Primary BK monolayer cultures were inoculated with the viral isolates, and the efficiency of plaque formation was compared at 32° C (a permissive temperature for the recombinants) and 39° C (a restrictive temperature for the recombinants).

The clinical response of the Patients to the recombinants is set out in Table 2 below.

TABLE 2

Response of seronegative volunteers to its recombinants of influenza A (H3N2) virus.

| | | | | | | | Influenzal illness with cough and sputum production | | |
|---|---|---|---|---|---|---|---|---|---|
| Recombinant or wild-type virus | Dose of virus per man ($TCID_{50}$) | Shut-off temperature* | No. of men | No. infected † | Coryza ‡ | Coryza plus pharyngitis and malaise | Mild influenzal illness § | | Fever (range) | Any illness |
| ts-1 [A] | $10^{5.5}$ | 37 C | 13 | 0 | 0 | 0 | 0 | 0 | 0 | 0 |
| ts-1 [E] | $10^{6.0}$ | 38 C | 17 | 16 | 4 | 1 | 0 | 0 | 0 | 5 |
| ts-2 [C] * | $10^{5.5}$ | 39 C | 8 | 8 | 0 | 5 | 3 | 0 | 2(37.5 C) | 8 |
| BK-4 ‖ | $10^{5.0}$ | >40 C | 21 | 19 | 0 | 3 | 4 | 7 | 8(37.5 C–38.8 C) | 14 |
| HEK-2 # | $10^{4.5}$ | >40 C | 7 | 7 | 0 | 0 | 1 | 5 | 6(37.7 C–40.2 C) | 6 |

*Lowest temperature at which a 100-fold decrease in efficiency of plaque formation was observed.
† Recovery of virus and/or a fourfold or greater rise in serum and/or nasal-secretion neutralizing antibody.
‡ Coryza=nasal stuffiness, rhinorrhea, sneezing.
§ Mild influenzal illness=coryza, pharyngitis, malaise, plus two of the following: chills, sweating, photophobia, or headache.
‖ BK=passaged in primary bovine-kidney cells (wild-type virus).
HEK=passaged in human embryonic-kidney cells (wild-type virus).
* ts-2[C]=an additional virus strain indirectly related to the present tests.

EXAMPLE 2

Five to seven weeks after administration of the recombinants, the volunteers described in Example 1 were challenged with a wild-type virus to determine whether the ts viruses had induced homologous resistance. The protection against wild-type virus exhibited by the men who had received the ts-1[E] recombinant five weeks previously is shown in Table 3 below.

These men were challenged with the suspension of HEK-2 wild-type virus, which produced febrile influenzal illness in six of seven seronegative men. None of the previous recipients of the ts-1[E] recombinant developed any signs or symptoms after challenge with wild-type virus, nor did they shed virus; however, seven of the 12 men were infected as indicated by a serologic response.

The ts-1[E] recombinant appeared to possess a number of properties desirable for a candidate strain for use in a live vaccine. Pertaining to communicability, the studies are set out in Table 4 below.

TABLE 3

Response to wild-type influenza A (H3N2) virus of volunteers previously given recombinant virus.

| Study | Mutant used for initial infection | Virus used for challenge | No. of volunteers | No. shedding virus | No. infected* | Average no. of days of virus shedding † | Percentage of inoculated cultures yielding virus ‡ | Temperature ≥99.4 F | Common cold | Influenzal illness | Any illness |
|---|---|---|---|---|---|---|---|---|---|---|---|
| 1 | ts-2 [C] | Wild-type BK-4 ($10^5$ $TCID_{50}$) | 5 | 3 | 5 | 0.8 ⎤ | 4 ⎤ | 0 | 1 | 0 | 1 |
| 1 | None | Wild-type BK-4 ($10^5$ $TCID_{50}$) | 21 | 18 | 19 | 3.8 ⎦ | 29 ⎦ | 8 | 3 | 11 | 14 |
| 2 | ts-1 [E] | Wild-type HEK-2 ($10^{4.5}$ $TCID_{50}$) | 12 | 0 | 7 | 0 ⎤ | 0 ⎤ | 0 | 0 | 0 | 0 ⎤ |
| 2 | None | Wild-type HEK-2 ($10^{4.5}$ $TCID_{50}$) | 7 | 7 | 7 | 4.3 ⎦ | 39 ⎦ | 6 | 0 | 6 | 6 ⎦ |

Note.
Solid brackets=statistically significant difference between values at ends of brackets (Student's t-test, P<.01).
Dotted brackets=statistically significant difference between values at ends of brackets (Fisher exact test, P<.01).
*Recovery of virus and/or a fourfold or greater rise in serum and/or nasal-secretion neutralizing antibody.
† Each volunteer tested daily for 10 days after challenge.
‡ Each nasopharyngeal washing tested in four monkey-kidney cultures.

TABLE 4

Lack of communicability of influenza A (H3N2) ts-1 [E] recombinant.

| | | No. with indicated response | | | | | | | |
|---|---|---|---|---|---|---|---|---|---|
| | | No. with neutralizing antibody ≤1:4 before challenge | Shedding of virus* | Development of fourfold or greater rise in neutralizing antibody | | Reciprocal of geometric mean neutralizing antibody titer on indicated day | | | |
| | | | | | | Serum | | Nasal wash † | |
| No. of volunteers | Virus administered | | | Serum | Nasal wash | 0 | 28 | 0 | 28 |
| 10 | Yes ‡ | 6 | 7 | 9 | 8 | 5 | 81 | 2 | 11 |
| 7 | No | 5 | 0 | 0 | 0 | 5 | 4 | 3 | 3 |

*Nasopharyngeal-wash specimens were tested daily for 10 days for virus.
† Adjusted to 20 mg IgA/100 ml (using a serum IgA standard).
‡ Each volunteer inoculated intranasally with $10^6$ $TCID_{50}$ of influenza A (H3N2) ts-1 [E].

EXAMPLE 3

Preparation of the Influenza A/Hong Kong/1968-ts-1[A] Virus

The influenza A virus was prepared in an identical manner as the influenza A/Hong Kong/1968-ts-1[E] virus (page 8, specification). However, it was clearly different from the Hong Kong/1968-ts-1[E] virus in that the Hong Kong/1968-ts-1[A] virus possesses a lower shut-off temperature (37° versus 38°) and possesses a ts lesion in a different complementation group (Table 1). This virus serves as a donor of ts lesions to future wild-type influenza A viruses.

EXAMPLE 4

Preparation of Double Recombinant 10B Virus

The influenza Double Recombinant 10B virus was prepared in primary bovine kidney cell culture by mixed infection of the following two temperature-sensitive influenza A parent viruses:

(1) ts parent virus A: Influenza A/Ann Arbor/Marton/1943-R11 (HON2) ts virus. This virus is a recombinant virus of the influenza A/Ann Arbor/Marton/1943 wild-type virus and the influenza A/Hong Kong/1968-ts-1[E] virus. It possesses the same ts lesions and shut-off temperature as the Hong Kong/1968-ts-1[E] virus and the hemagglutinin of the HON1 wild-type virus parent.

(2) ts parent virus B: Influenza A/Hong Kong/1968-ts-304. This ts parent virus was produced by chemical mutagenesis with 5-fluorouracil in an analogous manner to the influenza A/Great Lakes/1965-ts-1 (H2N2) virus (page 8, specification).

ts virus was isolated from the recombinant progeny of the above cross in an analogous manner as the isolation of the influenza A/Hong Kong/1968-ts-1-8 E] virus parent (page 8, specification). As seen in Table 1, the double recombinant 10B virus contains two ts lesions, one in complementation group 1 from the HON2 R11 ts parent and one in complementation group 4 from the ts 304 virus. This virus has been shown to be attenuated and genetically stable in hamsters and serves as a donor of its ts lesion to new wild-type influenza A viruses.

In the present specification and claims the term "donor virus" is intended to mean a directly mutagenized virus or a recombinant virus such as described in Examples 2, 3, and 4.

We claim:

1. A composition consisting of a virus and a compatible carrier wherein said virus consists of a temperature-sensitive (ts) recombinant mutant virus produced by growth of an influenza A virus in the presence of 5-fluorouracil to produce a chemically mutagenized and temperature-sensitive virus which is the donor of a defined genetic defect and which is mated with a virulent wild-type A virus of a different antigenic type to produce the recombinant mutant virus.

2. The composition according to claim 1 wherein the temperature-sensitive donor virus is influenza A/Hong Kong/1968-ts-1(A).

3. The composition according to claim 1 wherein the temperature-sensitive donor virus is influenza A Double recombinant 10B.

4. The composition according to claim 1 wherein the temperature-sensitive donor virus is influenza A/Hong Kong/1968-ts-1(E).

5. A method of producing a temperature-sensitive (ts) recombinant mutant virus which has a shut-off temperature of about 37°–38° C which comprises growing an influenza A virus in the presence of 5-fluorouracil to produce a donor virus possessing a temperature-sensitive genetic defect and mating said donor virus with a virulent wild-type A virus of a different antigenic type to produce a ts recombinant mutant virus of the new antigenic type.

* * * * *

UNITED STATES PATENT OFFICE
CERTIFICATE OF CORRECTION

PATENT NO. : 3,992,522
DATED : November 16, 1976
INVENTOR(S) : Robert M. Chanock and Brian R. Murphy It is certified that error appears in the above—identified patent and that said Letters Patent are hereby corrected as shown below:

At column 5, line 15, "375°C" should be --37°C--.

At column 9, line 33, "ts-1-8 E]" should be -- ts-1[E] --

Signed and Sealed this

Fifteenth Day of February 1977

[SEAL]

Attest:

RUTH C. MASON
*Attesting Officer*

C. MARSHALL DANN
*Commissioner of Patents and Trademarks*